United States Patent [19]

Muccioli et al.

[11] Patent Number: 6,124,263
[45] Date of Patent: Sep. 26, 2000

[54] TREATMENT OF TUMORS BY ADMINISTRATION OF GROWTH HORMONE RELEASING COMPOUNDS AND THEIR ANTAGONISTS

[75] Inventors: Gianpiero Muccioli, Rivalba; Mauro Papotti; Ezio Ghigo, both of Turin, all of Italy; Romano Deghenghi, Le-Vesinet, France

[73] Assignee: Asta Medica AG, Radebeul, Germany

[21] Appl. No.: 09/192,406

[22] Filed: Nov. 16, 1998

[51] Int. Cl.[7] ..................................................... A61K 38/00
[52] U.S. Cl. ................................................. 514/17; 514/2
[58] Field of Search ................................ 514/278, 2, 17; 546/17; 530/310, 311

[56] References Cited

U.S. PATENT DOCUMENTS 5,552,520  9/1996  Kim et al. ................................ 530/311

*Primary Examiner*—Elli Peselev
*Attorney, Agent, or Firm*—Pennie & Edmonds LLP

[57] ABSTRACT

A method for treating a tumor in a mammal by administering a growth hormone releasing compound or an antagonist thereof in an amount effective to reduce or inhibit proliferation of tumorigenic cells in the mammal. In particular, the tumors to be treated include lung, mammary, thyroid or pancreas tumors. The preferred compounds are certain peptides that contain methyl tryptophan and lysine units.

16 Claims, No Drawings

TREATMENT OF TUMORS BY ADMINISTRATION OF GROWTH HORMONE RELEASING COMPOUNDS AND THEIR ANTAGONISTS

FIELD OF THE INVENTION

The invention relates to a method for reducing the proliferation of carcinoma cells by administration of growth hormone releasing peptides and antagonists thereof.

BACKGROUND OF THE INVENTION

Growth hormone (GH) secretion is regulated by two hypothalamic peptides: GH-releasing hormone (GHRH), which exerts stimulatory effect on GH release and somatostatin which exhibits an inhibitory influence. In the last few years, several investigators have demonstrated that GH secretion can also be stimulated by synthetic oligopeptides termed GH-releasing peptides (GHRP) such as hexarelin and various hexarelin analogs (Ghigo et al., European Journal of Endocrinology, 136, 445–460, 1997). These compounds act through a mechanism which is distinct from that of GHRH (C. Y. Bowers, in "Xenobiotic Growth Hormone Secretagogues", Eds. B.Bercu and R. F. Walker, Pg. 9–28, Springer-Verlag, New York 1996) and by interaction with specific receptors localized in the hypothalamus and pituitary gland ((a) G. Muccioli et al., Journal of Endocrinology, 157, 99–106, 1998; (b) G. Muccioli, "Tissue Distribution of GHRP Receptors in Humans", Abstracts IV European Congress of Endocrinology, Sevilla, Spain, 1998). Recently it was demonstrated that GHRP receptors are present not only in the hypothalamo-pituitary system but even in various human tissues not generally associated with GH release (G. Muccioli et al., see above (a)).

GHRPs and their antagonists are described, for example, in the following publications: C. Y. Bowers, supra, R. Deghenghi, "Growth Hormone Releasing Peptides", ibidem, 1996, pg. 85–102; R. Deghenghi et al., "Small Peptides as Potent Releasers of Growth Hormone", J. Ped. End. Metab., 8, pg. 311–313, 1996; R. Deghenghi, "The Development of Impervious Peptides as Growth Hormone Secretagogues", Acta Paediatr. Suppl., 423, pg. 85–87, 1997; K. Veeraraganavan et al., "Growth Hormone Releasing Peptides (GHRP) Binding to Porcine Anterior Pituitary and Hypothalamic Membranes", Life Sci., 50, Pg. 1149–1155, 1992; and T. C. Somers et al., "Low Molecular Weight Peptidomimetic Growth Hormone Secretagogues, WO 96/15148 (May 23, 1996).

SUMMARY OF THE INVENTION

The present invention relates to a method for treating a tumor in a mammal which method comprises administering to a mammal in need of such treatment an effective amount of a growth hormone releasing peptide (GHRP) or an antagonist thereof. Alternatively, the compounds used according to the invention can be defined as growth hormone secretagogues or antagonists thereof. The amounts of these compounds are effective to reduce or inhibit the proliferation of tumorigenic cells in the mammal. In an alternative embodiment, these compounds are specified by the feature that they displace the radioactive marker $^{125}$I-Tyr-Ala-His-D-Mrp-Ala-Trp-D-Phe-Lys-NH$_2$ ($^{125}$I-Tyr-Ala-Hexarelin) from a tumor containing tissue of the mammal.

The compounds disclosed herein exhibit binding to tumorigenic tissue and have been found to act on a specific receptor after administration, thus imparting a decrease in the number of tumorigenic cells. Preferably, treated tumors are lung, mammary, thyroid or pancreas tumors.

The above mentioned compounds include certain known compounds (cf. above), but other compounds useful in the invention are not previously published and include a spirolactam, bicyclic or tricyclic peptidomimetic unit. One common feature for all compounds useful in the invention is that at least one lysine unit is present.

DETAILED DESCRIPTION OF THE PREFERRED EMBODIMENTS

In this description, the following abbreviations are used: D is the dextro enantiomer, GH is growth hormone, Mrp is 2-Methyl-Trp, IMA is imidazolylacetyl, GAB is γ-amino butyryl, INIP is isopecotinyl, AIB is amino isobutyryl, Nal is β-naphthylalanine, TXM is tranexamyl, i.e. 4-(aminomethyl)-cyclohexane carbonyl, D-HNH is D-1,2,3,4,5,6-hexahydro-norharman-3-carboxylate, HAIC is (2S,5S)-5-amino-1,2,4,5,6,7-hexahydro-azepino[3,2,1-hi]indole-4-one-2-carboxylate, ATAB is 2-R-(2β,5β,8β)-8-amino-7-oxo-4-thia-1-aza-bicyclo[3.4.0]nonan-2-carboxylate, and Ala, Lys, Phe, Trp, His, Thr, Cys, Tyr, Leu and Ile are the amino acids alanine, lysine, phenylalanine, tryptophan, histidine, threonine, cysteine, tyrosine, leucine and isoleucine, respectively.

In one embodiment of the invention, useful compounds to be administered are of the general formula I:

$$AA^1\text{-}AA^2\text{-}AA^3\text{-}AA^4\text{-}Lys\text{-}R \tag{I}$$

in which:

AA$^1$ is IMA, GAB, INIP, TXM, AIB, HIs-D-Trp-, His-D-Mrp, Thr-D-Trp,

Thr-D-Mrp, D-Thr-D-Trp, D-Thr-D-Mrp, D-Ala-D-Nal, IMA-D-Trp, IMA-D-Mrp,

D-Thr-His-D-Trp, D-Thr-His-D-Mrp, Cys-Tyr-GAB, Ala-His-Trp,

Ala-His-D-Mrp, Tyr-Ala-His-D-Trp, Tyr-Ala-His-D-Mrp, D-Ala-D-Trp, or D-Ala-D-Mrp;

AA$^2$ is Ala, D-Nal, D-Lys, D-Mrp, or Trp;

AA$^3$ is D-Trp, D-Nal, D-Trp, Mrp, D-Mrp, Phe, or D-Phe;

AA$^4$ is D-Trp, Mrp, D-Mrp, Phe, or D-Phe; and

R is —NH$_2$, Thr-NH$_2$, or D-Thr-NH$_2$.

The compounds containing a D-Mrp unit are preferred.

In an another embodiment, the useful compounds include those described in U.S. patent application Ser. No. 09/089,954, filed Jun. 3, 1998. These compounds are peptides of the general formula II:

$$A\text{---}B\text{---}D\text{-}Mrp\text{-}C\text{---}E \tag{II}$$

in which:

A is H or Tyr;

B is a spirolactam of the general formula III (III)

where R$^1$ is H or Tyr, R$^2$ represents the side chain of any one naturally occurring amino acid, and the configuration at * is (R), (S) or a mixture thereof; a tricyclic compound of the formula IV

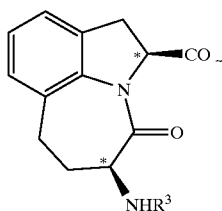
(IV)

where $R^3$ is H or Tyr and the configuration at * is (R), (S) or a mixture thereof; a bicyclic compound of the formula V

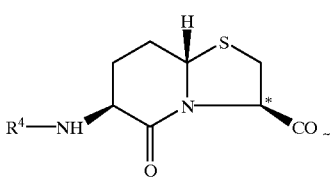
(V)

where $R^4$ is H or Tyr and the configuration at * is (R), (S) or a mixture thereof;

D-Mrp is Dextro-2-Methyl-Trp;

C is Trp-Phe-Lys, D-Trp-Phe-Lys, Mrp-Phe-Lys, D-Mrp-Phe-Lys, Trp-Lys,

D-Trp-Lys, Mrp-Lys, D-Mrp-Lys, Ala-Trp-D-Phe-Lys, Ala-Mrp-D-Phe-Lys,

Ala-D-Mrp-D-Phe-Lys, D-Lys-Trp-D-Phe-Lys, D-Lys-Mrp-D-Phe-Lys,

D-Lys-D-Mrp-D-Phe-Lys, or a tricyclic compound of the formula VI

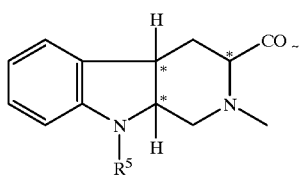
(VI)

where $R^5$ is H or $SO_2Me$ and the configurations at * are either (R), (S) or a mixture thereof; and E is Lys-$NH_2$ or —$NH_2$, provided that E is Lys-$NH_2$, when C is the previously defined tricyclic compound VI.

In accordance with the present invention, it has been found that both GH liberating compounds and compounds that do not liberate GH are useful for the treatment of tumors. Preferably the tumor to be treated according to the invention is a lung, mammary, thyroid or pancreas tumor.

Specifically preferred GH liberating compounds of the general formula I include the following:

His-D-Trp-Ala-Trp-D-Phe-Lys-$NH_2$,
His-D-Trp-Ala-Mrp-D-Phe-Lys-$NH_2$,
D-Thr-His-D-Mrp-Ala-Trp-D-Phe-Lys-$NH_2$,
Thr-D-Mrp-Ala-Trp-D-Phe-Lys-$NH_2$,
IMA-D-Mrp-D-Trp-Phe-Lys-$NH_2$,
IMA-D-Mrp-D-Nal-Phe-Lys-$NH_2$,
GAB-D-Mrp-D-Mrp-D-Mrp-Lys-$NH_2$,
D-Ala-D-Nal-Ala-Trp-D-Phe-Lys-$NH_2$,
INIP-D-Nal-D-Nal-Phe-Lys-$NH_2$,
INIP-D-Nal-D-Trp-Phe-Lys-$NH_2$,
IMA-D-Mrp-Ala-Trp-D-Phe-Lys-$NH_2$,
INIP-D-Mrp-D-Trp-Phe-Lys-$NH_2$,
INIP-D-Mrp-D-Nal-Phe-Lys-$NH_2$,
GAB-D-Mrp-D-Trp-Phe-Lys-$NH_2$,
TXM-D-Mrp-D-Trp-Phe-Lys-$NH_2$,
GAB-D-Mrp-Mrp-Phe-Lys-$NH_2$,
Ala-His-D-Mrp-Ala-Trp-D-Phe-Lys-$NH_2$,
His-D-Mrp-Ala-Trp-D-Phe-Lys-Thr-$NH_2$,
His-D-Mrp-Ala-Trp-D-Phe-Lys-$NH_2$,
D-Thr-D-Mrp-Ala-Trp-D-Phe-Lys-$NH_2$,
GAB-D-Mrp-D-Nal-Phe-Lys-$NH_2$,
GAB-D-Mrp-D-Mrp-Mrp-Lys-$NH_2$,
Cys-Tyr-GAB-D-Mrp-D-Mrp-Mrp-Lys-$NH_2$,
Tyr-Ala-His-D-Mrp-Ala-Trp-D-Phe-Lys-$NH_2$, and
D-Ala-D-Mrp-Ala-Trp-D-Phe-Lys-$NH_2$, while preferred compounds of the general formula I that do not liberate GH include:

His-D-Trp-D-Lys-Trp-D-Phe-Lys-$NH_2$,
His-D-Mrp-D-Lys-Trp-D-Phe-Lys-$NH_2$,
His-Ala-D-Trp-Lys-Mrp-D-Phe-Lys-$NH_2$,
His-D-Mrp-D-Lys-Mrp-D-Phe-Lys-$NH_2$,
His-Ala-D-Trp-Ala-Mrp-D-Phe-Lys-$NH_2$, and
His-D-Trp-Ala-Mrp-D-Phe-Lys-$NH_2$.

The preferred compounds of the general formula II include the following:

[S,S-Spiro(Pro-Leu)]-D-Mrp-D-Trp-Phe-Lys-$NH_2$,
[S,S-Spiro(Pro-Leu)]-D-Mrp-Mrp-Lys-$NH_2$,
[S,S-Spiro(Pro-Leu)]-D-Mrp-Ala-Trp-D-Phe-Lys-$NH_2$,
[S,S-Spiro(Pro-Leu)]-D-Mrp-D-Lys-Trp-D-Phe-Lys-$NH_2$,
Tyr-[S,S-Spiro(Pro-Leu)]-D-Mrp-D-Lys-Trp-D-Phe-Lys-$NH_2$,
[S,S-Spiro(Pro-Ile)]-D-Mrp-D-Lys-Trp-D-Phe-Lys-$NH_2$,
[S,S-Spiro(Pro-Leu)]-D-Mrp-D-HNH-($SO_2CH_3$)-Phe-Lys-$NH_2$,
HAIC-D-Mrp-D-Lys-Trp-D-Phe-Lys-$NH_2$, and
ATAB-D-Mrp-D-Lys-Trp-D-Phe-Lys-$NH_2$, where S,S-Spiro(Pro-Leu) and S,S-Spiro(Pro-Ile) is 4-Methyl-2S[6'-oxo-(5'-S)1',7'-diazaspiro[4,4]nonan-7'-yl-]pentanoate and 3-Methyl-2S[6'-oxo-(5'-S)1',7'-diazaspiro[4,4]nonan-7'-yl-]pentanoate, respectively.

These units have the formula

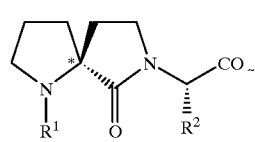
(III)

where $R^1$ is H and $R^2$ is the side chain of Leu or Ile (see P. Ward et al., J. Med. Chem., 33, 1848 (1990)). Also, the tricyclic compound HNH is obtained by conventional hydrogenation of the corresponding tetrahydro-norharman-3-carboxylic acids of the formula

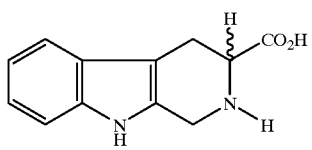

(VII)

The units according to the formulas III, IV, V and VI constitute peptidomimetic units which are advantageous in that they lock in a β-turn configuration thus mimicking natural amino acids.

Pharmaceutically acceptable salts of these compounds can be also used, if desired. Such salts include organic or inorganic addition salts, such as hydrochloride, hydrobromide, phosphate, sulfate, acetate, succinate, ascorbate, tartrate, gluconate, benzoate, malate, fumarate, stearate or pamoate salts.

All compounds can be conveniently synthesized according to the usual methods of peptide chemistry, such as by solid-phase peptide synthesis, as described by E. Atherton and R. C. Sheppard in "Solid Phase Peptide Synthesis", IRL Press at Oxford University Press, 1989, by solution-phase synthesis as described by J. Jones in "The Chemical Synthesis of Peptides", Clarendon Press, Oxford 1994, or by a combination of both solid- and solution-phase methods, as known in the art.

The solid-phase synthesis starts from the C-terminal end of the compounds. A suitable starting material can be prepared, for example, by attaching the required protected α-amino acid to a chloromethylated resin, a hydroxymethylated resin, a benzhydrylamine resin (BHA), or to a para-methyl-benzhydrylamine resin (p-Me-BHA). As an example, an available chloromethylated resin is BIOBEADS SX1 by BioRad Laboratories, Richmond, Calif. The preparation of the hydroxymethylated resin is described by Bodansky et al., Chem. Ind. (London), 38, 15997 (1966). The BHA resin is described by Pietta and Marshall, Chem. Comm., 650 (1970), and is commercially available by Peninsula Laboratories Inc., Belmont, Calif.

After the starting attachment, the protecting group of the α-amino acid can be removed by means of different acid reagents, such as trifluoroacetic acid (TFA) or hydrochloric acid (HCl) dissolved in organic solvents at room temperature. After the removal of the protecting group of the α-amino acid, the remaining protected natural amino acids or carboxylic acids corresponding to the units according to the general formulas III, IV, V and VI, which also constitute amino acids, can be coupled step by step in the desired order. Each protected amino acid can generally be reacted in excess of about three times using a suitable carboxyl activating group, such as dicyclohexylcarbodiimide (DCC) or diisopropylcarbodiimide (DIC) dissolved, for example, in methylene chloride ($CH_2Cl_2$), dimethylformamide (DMF) or their mixtures. After the desired aminoacidic sequence has been completed, the desired compound can be cleaved from the supporting resin by treatment with a reagent such as hydrogen fluoride (HF) which cleaves not only the compound from the resin, but also the protecting groups of lateral chains. When a chloromethylated resin is used, treatment with HF leads to the formation of a compound which has a terminal acid group and is present in free form. When a BHA or p-Me-BRA resin is used, the treatment with HF directly leads to the formation of a compound which has a terminal amide group and is present in free form.

Medicaments useful for treating tumors in a mammal, including a human, can comprise a compound according to the present invention or a pharmaceutically acceptable salt thereof, or combinations of compounds according to the present invention or pharmaceutically acceptable salts thereof, optionally in admixture with a carrier, excipient, vehicle, diluent, matrix, or delayed release coating. Examples of such carriers, excipients, vehicles, and diluents, can be found in Remington's Pharmaceutical Sciences, 18th Edition, A. R. Gennaro, Ed., Mack Publishing Company, Easton, Pa, 1990.

Any of the compounds according to the present invention can be formulated by the skilled in the art to provide medicaments which are suitable for parenteral, buccal, rectal, vaginal, transdermal, pulmonary or oral routes of administration.

The type of formulation of the medicament containing the compound can be selected according to the desired rate of delivery. For example, if the compounds are to be rapidly delivered, the nasal or intravenous route is preferred.

The medicaments can be administered to mammals, including humans, at a therapeutically effective dose which can be easily determined by one of skill in the art and which can vary according to the specie, age, sex and weight of the treated patient or subject as well the route of administration. For example, in humans, when intravenously administered, the preferred dose falls in the range from about 1 μg to about 25 μg of total compound per kg of body weight. When orally administered, higher amounts are generally necessary. For example, in humans for the oral administration, the dosage level is typically from about 30 μg to about 1000 μg of total compound per kg of body weight. The exact level can be easily determined empirically based on the above disclosure.

EXAMPLES

The following examples illustrate the efficacy of the most preferred compounds used in the tumor treatment of this invention.

1. Materials and Methods a) Chemicals

Hexarelin (His-D-Mrp-Ala-Trp-D-Phe-Lys-$NH_2$), Ala-Hexarelin (Ala-His-D-Mrp-Ala-Trp-D-Phe-Lys-$NH_2$), Tyr-Ala-Hexarelin (Tyr-Ala-His-D-Mrp-Ala-Trp-D-Phe-Lys-$NH_2$), MK0677 (N-[1(R) ([1,2-dihydro-1-methanesulfonylspiro-(3H-indole, 3,4'-piperidin)-1'yl]-2-(phenylmethoxy)ethyl]-2-amino-methylpropanamide-methanesulfonate), EP80317 (HAIC-D-Mrp-D-Lys-Trp-D-Phe-Lys-$NH_2$) and D-$(Lys)_3$-GHRP6 (His-D-Trp-D-Lys-Trp-D-Phe-Lys-$NH_2$) were supplied by Europeptides (Argenteuil, France). Human GHRH (GHRH 1-44) and somatostatin (somatostatin 1-14) were purchased from Bachem (Bubendorf, Switzerland). Human recombinant epidermal growth factor (EGF) and all tissue culture reagents were purchased from Sigma Chemical Co. (St. Louis, Mo., USA). $^3$H-Thymidine was purchased from Pharmacia-Amersham Italia (Milan, Italy).

b) Human tissues

Surgical tumor specimens were collected from the Department of Biomedical Sciences and Human Oncology (Division of Pathology) of the University of Turin. A tumor fragment adjacent to that used for histopathological diagnosis was immediately frozen at −80° C. and stored for 2 to 60 months until further processed for binding studies. Samples of 13 invasive breast carcinoma (10 ductal and 3 lobular), 14 non-endocrine lung carcinomas (5 squamous cell and 9 adenocarcinomas), 11 endocrine tumors of the lung, 9 endocrine tumors of the pancreas and 12 thyroid carcinomas (7 of follicular origin and 5 of medullary origin)

were used. Non-neoplastic normal tissues of the corresponding organs were also analysed in parallel with the individual tumors.

c) Tumor cell lines

Human lung carcinoma cells (CaLu1), T47D and MDA-MB231, respectively, human oestrogen dependent and oestrogen independent breast cancer cell lines were purchased from the ATCC (Rockville, Md., USA). Cells were routinely cultured in 25 cm³ flasks at 37° C., 5% $CO_2$ and 95% humidified atmosphere in RPMI supplemented with 10% FCS, penicillin-streptomycin and fungizone. When a subconfluent state was reached, cells were detached from the flasks with trypsin/EDTA.

d) GHRP receptor assay

GHRP receptors were measured on tumor membranes as described in G. Muccioli et al., Journal of Endocrinology, 157, 99–106, 1998, using $^{125}$I-Tyr-Ala-Hexarelin as a ligand. Specific binding was calculated as the difference between binding in the absence and in the presence of excess unlabelled Tyr-Ala-Hexarelin and expressed as a percentage of the radioactivity added. Saturation and competition binding studies were analyzed with the GraphPAD Prism 2 program (GraphPAD Software, San Diego, Calif., USA).

e) Cell proliferation studies

DNA synthesis was evaluated by $^3$H-thymidine incorporation as described in G. Muccioli et al., Journal of Endocrinology, 153, 365–371, 1997. Starved cells were incubated with medium alone (basal) or EGF (1 ng/ml) in the absence or in the presence of different concentrations (from $10^{-8}$ to $10^{-6}$ mol/l) of Hexarelin, Ala-Hexarelin, Tyr-Ala-Hexarelin, MK0677, (D-Lys)$_3$-GHRP6 or EP80317. After incubation for 20 hours, $^3$H-thymidine was added and incubation was continued for a further 4 hours. The reaction was halted and the cells were harvested onto glass-fiber filter strips. Incorporation of $^3$H-thymidine was measured in a scintillation counter.

Cell growth studies were carried out as described in P.Cassoni et al., Virchows Archiv, 425, 467–472, 1994. Cells were seeded in triplicate in 24-multiwell plates at a density of 5,000–10,000 cells/ml. Twenty-four hours after plating the medium was changed. Hexarelin or Ala-Hexarelin were added where requested at concentrations ranging from $10^{-8}$ to $10^{-6}$ mol/l. The medium was changed every 48 hours. Cells were counted at 48 and 72 or 96 hours of treatment in a double blind analysis by two independent investigators using a haemocytometer.

f) Statistical analysis

Data were expressed as means (FIGS. 1 and 2) or means±S.E.M. (FIGS. 3 to 7) unless otherwise specified. Statistical significance was determined using Mann-Whitney test (FIGS. 1 to 3) or by one-way ANOVA (FIGS. 4 to 7). All experiments were carried out at least in triplicate.

2. Results a) Identification of receptors for GHRP and their antagonists in different human tumors FIG. 1 shows the distribution of radiolabelled Tyr-Ala-Hexarelin binding to membranes from different endocrine and non-endocrine human tumors of various origins (*P<0.01 vs. the corresponding non-tumoral tissue). Non-endocrine tumors of the lung and breast, as well as endocrine carcinomas of the pancreas and thyroid (follicular type) showed a median specific binding value which was statistically higher than that found in the corresponding non tumoral normal tissue. In contrast, no difference in the specific binding values was observed between normal tissue and endocrine tumors of the lung or thyroid (medullary type).

b) Biochemical characteristics of receptors for GHRP and their antagonists

To determine whether the binding of $^{125}$I-Tyr-Ala-Hexarelin to tumor membranes shows the properties typical of ligand-receptor interaction, the binding of radiotracer was investigated in more detail in a non-endocrine carcinoma of lung origin which displayed the highest specific binding value. FIG. 2 reports the binding of $^{125}$I-Tyr-Ala-Hexarelin to tumor membranes as a function of increasing concentrations of radioligand. This study revealed evidence of saturable specific binding and Scatchard analysis (upper panel) indicated the presence of a single class of high affinity sites.

The specificity of $^{125}$I-Tyr-Ala-Hexarelin binding was established by determining the ability of different compounds to compete with the radioligand for the tumoral binding sites (cf. FIG. 3). The binding of radiotracer was displaced in a dose-dependent fashion by Hexarelin, Ala-Hexarelin, Tyr-Ala-Hexarelin and GHRP antagonists such as D-(Lys)$_3$-GHRP6 and EP 80317, an (Amino-azepino-indol)$_1$-D-(Lys)$_3$ derivative of Hexarelin which does not release GH in neonatal rats. A negligible displacement was observed in the presence of MK0677, a non-peptidyl GHRP mimetic that bind to pituitary GHRP receptors. In contrast, no competition was observed in the presence of GHRH or somatostatin.

c) Effect of GHRP and their antagonists on $^3$H-thymidine incorporation

Hexarelin at $10^{-6}$ mol/l was able to inhibit both basal and the EGF-stimulated $^3$H-thymidine incorporation in human cells of lung carcinoma (cf. FIG. 4; *P<0.05, **P<0.01 vs. control). This antiproliferative effect was also observed when the cells were incubated in the presence of $10^{-6}$ mol/l Ala-Hexarelin, Tyr-Ala-Hexarelin or GHRP antagonists such as (D-Lys)$_3$-GHRP6 and EP80317. In contrast, a slight inhibition was observed in the presence of MK0677. Experiments using increasing concentrations of Hexarelin, Ala-Hexarelin, Tyr-Ala-Hexarelin, (D-Lys)$_3$-GHRP6 and EP80317 (cf. FIG. 5) revealed that these compounds inhibited the proliferative effect of EGF on human lung carcinoma cells inhibited in a dose-dependent fashion. The EC$_{50}$ value was $5.6 \times 10^{-8}$ mol/l for EP80317, $6.5 \times 10^{-8}$ mol/l for Tyr-Ala-Hexarelin, $8 \times 10^{-8}$ mol/l for Hexarelin, $9 \times 10^{-8}$ mol/l for (D-Lys)$_3$-GHRP6 and $1 \times 10^{-7}$ mol/l for Ala-Hexarelin.

d) Effect of GHRP on cell growth

In human lung carcinoma cells Hexarelin at $10^{-8}$ mol/l caused a decrease in cell number compared with the control with a significant effect (−47%) only after 96 hours. This effect further increased at $10^{-7}$ mol/l and $10^{-6}$ mol/l and was observed at any time point tested (cf. FIG. 6; P<0.001; *P<0.0001 vs. control).

In human breast cancer T47D cells Hexarelin at $10^{-8}$ mol/l caused a decrease in cell number compared with control with a significant effect (−54%) only after 96 hours. This effect further increased at $10^{-7}$ mol/l and $10^{-6}$ mol/l and was observed at any time point tested (cf. FIG. 7a; P<0.001; *P<0.0001 vs. control). A similar antiproliferative effect was also displayed by Ala-Hexarelin on these tumor cells (cf. FIG. 7b; P<0.001; *P<0.0001 vs. control).

In human breast cancer MDA-MB231 cells Hexarelin at $10^{-8}$ mol/l caused a decrease in cell number compared with control with a significant effect (−33%) only after 72 hours. This effect further increased at $10^{-7}$ mol/l and $10^{-6}$ mol/l and was observed at any time point tested (cf. FIG. 8a; *P<0.01; P<0.001; *P<0.0001 vs. control). A similar antiproliferative effect was also displayed by Ala-Hexarelin on these tumor cells (cf. FIG. 8b; *P<0.01; P<0.001; *P<0.0001 vs. control).

These results demonstrate that synthetic growth hormone releasing peptides and their antagonists inhibit the growth of human carcinoma cells in vitro. The antiproliferative effect is mediated by a specific receptor.

What is claimed is:

1. A method of treating a tumor in a mammal which method comprises administering to a mammal in need of said treatment a growth hormone releasing peptide or an antagonist thereof in an amount effective to reduce or inhibit proliferation of tumorigenic cells, wherein the growth hormone releasing peptide or antagonist administered to the mammal displaces the radioactive marker $^{125}$I-Tyr-Ala-His-D-Mrp-Ala-Trp-D-Phe-Lys-NH$_2$ from a tumor containing tissue of said mammal.

2. The method of claim 1, wherein the tumor is a lung or mammary tumor.

3. A method of treating a tumor in a mammal which method comprises administering to a mammal in need of said treatment a growth hormone-secretagogue or an antagonist thereof in an amount effective to reduce or inhibit proliferation of tumorigenic cells, wherein the growth hormone secretagogue or antagonist administered to the mammal displaces the radioactive marker $^{125}$I-Tyr-Ala-His-D-Mrp-Ala-Trp-D-Phe-Lys-NH$_2$ from a tumor containing tissue of said mammal.

4. The method of claim 3, wherein the tumor is a lung or mammary tumor.

5. A method of treating a mammal having a tumor provided with a receptor for growth hormone secretagogues which method comprises administering to a mammal in need of said treatment a growth hormone releasing peptide or an antagonist thereof in an amount effective to bind to the receptor to reduce or inhibit proliferation of tumorigenic cells.

6. The method of claim 5, wherein the tumor is a lung or mammary tumor.

7. A method of treating a mammal having a tumor provided with a receptor for growth hormone releasing peptides which method comprises administering to a mammal in need of said treatment a growth hormone secretagogue or an antagonist thereof in an amount effective to bind to the receptor to reduce or inhibit proliferation of tumorigenic cells.

8. The method of claim 7, wherein the tumor is a lung or mammary tumor.

9. A method of treating a tumor in a mammal which method comprises administering to a mammal in need of said treatment a therapeutically effective amount of a compound to reduce or inhibit proliferation of tumorigenic cells, wherein the compound is selected from the group consisting of a) compounds of formula I

in which:

AA$^1$ is IMA, GAB, INIP, TXM, AIB, His-D-Trp-, His-D-Mrp, Thr-D-Trp, Thr-D-Mrp, D-Thr-D-Trp, D-Thr-D-Mrp, D-Ala-D-Nal, IMA-D-Trp, IMA-D-Mrp, D-Thr-His-D-Trp, D-Thr-His-D-Mrp, Cys-Tyr-GAB, Ala-His-Trp, Ala-His-D-Mrp, Tyr-Ala-His-D-Trp, Tyr-Ala-His-D-Mrp, D-Ala-D-Trp, or D-Ala-D-Mrp;

AA$^2$ is Ala, D-Nal, D-Lys, D-Mrp, or Trp;

AA$^3$ is D-Trp, D-Nal, D-Trp, Mrp, D-Mrp, Phe, or D-Phe;

AA$^4$ is D-Trp, Mrp, D-Mrp, Phe, or D-Phe; and

R is —NH$_2$, Thr-NH$_2$, or D-Thr-NH$_2$; and b) compounds of formula II

in which:

A is H or Tyr;

B is a spirolactam of formula III

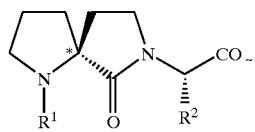

where R' is H or Tyr, R$^2$ represents the side chain of any one naturally occurring amino acid, and the configuration at * is (R), (S) or a mixture thereof; a tricyclic compound of the formula IV

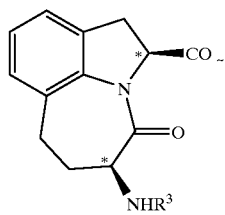

where R$^3$ is H or Tyr and the configuration at * is (R), (S) or a mixture thereof; a bicyclic compound of the formula V

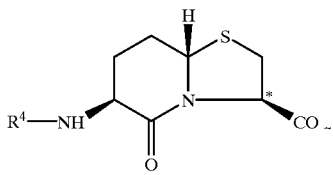

where R$^4$ is H or Tyr and the configuration at * is (R), (S) or a mixture thereof;

D-Mrp is Dextro-2-Methyl-Trp;

C is Trp-Phe-Lys, D-Trp-Phe-Lys, Mrp-Phe-Lys, D-Mrp-Phe-Lys, Trp-Lys,

D-Trp-Lys, Mrp-Lys, D-Mrp-Lys, Ala-Trp-D-Phe-Lys, Ala-Mrp-D-Phe-Lys,

Ala-D-Mrp-D-Phe-Lys, D-Lys-Trp-D-Phe-Lys, D-Lys-Mrp-D-Phe-Lys,

D-Lys-D-Mrp-D-Phe-Lys, or a tricyclic compound of the formula VI

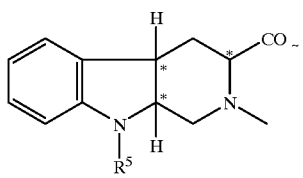

(VI)

where $R^5$ is H or $SO_2Me$ and the configurations at * are either (R), (S) or a mixture thereof; and E is Lys-$NH_2$ or —$NH_2$, provided that E is Lys-$NH_2$, when C is the previously defined tricyclic compound VI.

10. The method of claim 9, wherein the compound is
His-D-Trp-Ala-Trp-D-Phe-Lys-$NH_2$,
His-D-Trp-Ala-Mrp-D-Phe-Lys-$NH_2$,
D-Thr-His-D-Mrp-Ala-Trp-D-Phe-Lys-$NH_2$,
Thr-D-Mrp-Ala-Trp-D-Phe-Lys-$NH_2$,
IMA-D-Mrp-D-Trp-Phe-Lys-$NH_2$,
IMA-D-Mrp-D-Nal-Phe-Lys-$NH_2$,
GAB-D-Mrp-D-Mrp-D-Mrp-Lys-$NH_2$,
D-Ala-D-Nal-Ala-Trp-D-Phe-Lys-$NH_2$,
INIP-D-Nal-D-Nal-Phe-Lys-$NH_2$,
INIP-D-Nal-D-Trp-Phe-Lys-$NH_2$,
IMA-D-Mrp-Ala-Trp-D-Phe-Lys-$NH_2$,
INIP-D-Mrp-D-Trp-Phe-Lys-$NH_2$,
INIP-D-Mrp-D-Nal-Phe-Lys-$NH_2$,
GAB-D-Mrp-D-Trp-Phe-Lys-$NH_2$,
TXM-D-Mrp-D-Trp-Phe-Lys-$NH_2$,
GAB-D-Mrp-Mrp-Phe-Lys-$NH_2$,
Ala-His-D-Mrp-Ala-Trp-D-Phe-Lys-$NH_2$,
His-D-Mrp-Ala-Trp-D-Phe-Lys-Thr-$NH_2$,
His-D-Mrp-Ala-Trp-D-Phe-Lys-$NH_2$,
D-Thr-D-Mrp-Ala-Trp-D-Phe-Lys-$NH_2$,
GAB-D-Mrp-D-Nal-Phe-Lys-$NH_2$,
GAB-D-Mrp-D-Mrp-Mrp-Lys-$NH_2$,
Cys-Tyr-GAB-D-Mrp-D-Mrp-Mrp-Lys-$NH_2$,
Tyr-Ala-His-D-Mrp-Ala-Trp-D-Phe-Lys-$NH_2$, or
D-Ala-D-Mrp-Ala-Trp-D-Phe-Lys-$NH_2$.

11. The method of claim 9, wherein the compound is
His-D-Trp-D-Lys-Trp-D-Phe-Lys-$NH_2$,
His-D-Mrp-D-Lys-Trp-D-Phe-Lys-$NH_2$,
His-Ala-D-Trp-Lys-Mrp-D-Phe-Lys-$NH_2$,
His-D-Mrp-D-Lys-Mrp-D-Phe-Lys-$NH_2$,
His-Ala-D-Trp-Ala-Mrp-D-Phe-Lys-$NH_2$, or
His-D-Trp-Ala-Mrp-D-Phe-Lys-$NH_2$.

12. The method of claim 9, wherein the compound is
[S,S-Spiro(Pro-Leu)]-D-Mrp-D-Trp-Phe-Lys-$NH_2$,
[S,S-Spiro(Pro-Leu)]-D-Mrp-Mrp-Lys-$NH_2$,
[S,S-Spiro(Pro-Leu)]-D-Mrp-Ala-Trp-D-Phe-Lys-$NH_2$,
[S,S-Spiro(Pro-Leu)]-D-Mrp-D-Lys-Trp-D-Phe-Lys-$NH_2$,
Tyr-[S,S-Spiro(Pro-Leu)]-D-Mrp-D-Lys-Trp-D-Phe-Lys-$NH_2$,
[S,S-Spiro(Pro-Ile)]-D-Mrp-D-Lys-Trp-D-Phe-Lys-$NH_2$,
[S,S-Spiro(Pro-Leu)]-D-Mrp-D-HNH-($SO_2CH_3$)-Phe-Lys-$NH_2$,
HAIC-D-Mrp-D-Lys-Trp-D-Phe-Lys-$NH_2$, or
ATAB-D-Mrp-D-Lys-Trp-D-Phe-Lys-$NH_2$.

13. The method of claim 9, wherein the tumor is a lung or mammary tumor.

14. The method of claim 13, wherein the compound administered to the mammal displaces the radioactive marker $^{125}$I-Tyr-Ala-His-D-Mrp-Ala-Trp-D-Phe-Lys-$NH_2$ from a tumor containing tissue of said mammal.

15. The method of claim 6, wherein the compound administered to the mammal displaces the radioactive marker $^{125}$I-Tyr-Ala-His-D-Mrp-Ala-Trp-D-Phe-Lys-$NH_2$ from a tumor containing tissue of said mammal.

16. The method of claim 8, wherein the compound administered to the mammal displaces the radioactive marker $^{125}$I-Tyr-Ala-His-D-Mrp-Ala-Trp-D-Phe-Lys-$NH_2$ from a tumor containing tissue of said mammal.

* * * * *